United States Patent [19]

Schuler

[11] Patent Number: 4,470,533

[45] Date of Patent: Sep. 11, 1984

[54] SURGICAL INSTRUMENT FOR SUTURING TISSUES AND ORGANS

[75] Inventor: Michael Schuler, Edison, N.J.

[73] Assignee: Ethicon, Inc., Somerville, N.J.

[21] Appl. No.: 408,085

[22] Filed: Aug. 13, 1982

[51] Int. Cl.³ ............................................. A61B 17/00
[52] U.S. Cl. ...................................... 227/19; 227/135; 227/DIG. 1; 128/334 R
[58] Field of Search ................................... 128/334 R; 227/DIG. 1–DIG. 1 C, 19, 135, 155

[56] References Cited

U.S. PATENT DOCUMENTS

| | | | |
|---|---|---|---|
| 2,853,074 | 9/1958 | Olson | 227/19 |
| 2,891,250 | 6/1959 | Hirata | 227/19 |
| 3,244,342 | 4/1966 | Boorlakov et al. | 277/19 |
| 3,494,533 | 2/1970 | Green et al. | 227/DIG. 1 |
| 4,086,926 | 5/1978 | Green et al. | 128/334 R |
| 4,290,542 | 9/1981 | Fedotov et al. | 128/334 R |

FOREIGN PATENT DOCUMENTS 1278616  11/1961  France ............................ 128/334 R Primary Examiner—C. Fred Rosenbaum
Assistant Examiner—Gene B. Kartchner
Attorney, Agent, or Firm—Robert L. Minier

[57] ABSTRACT

The invention relates to surgical instruments used for suturing or stapling tissues and organs.

11 Claims, 9 Drawing Figures

U.S. Patent  Sep. 11, 1984  Sheet 1 of 3  4,470,533
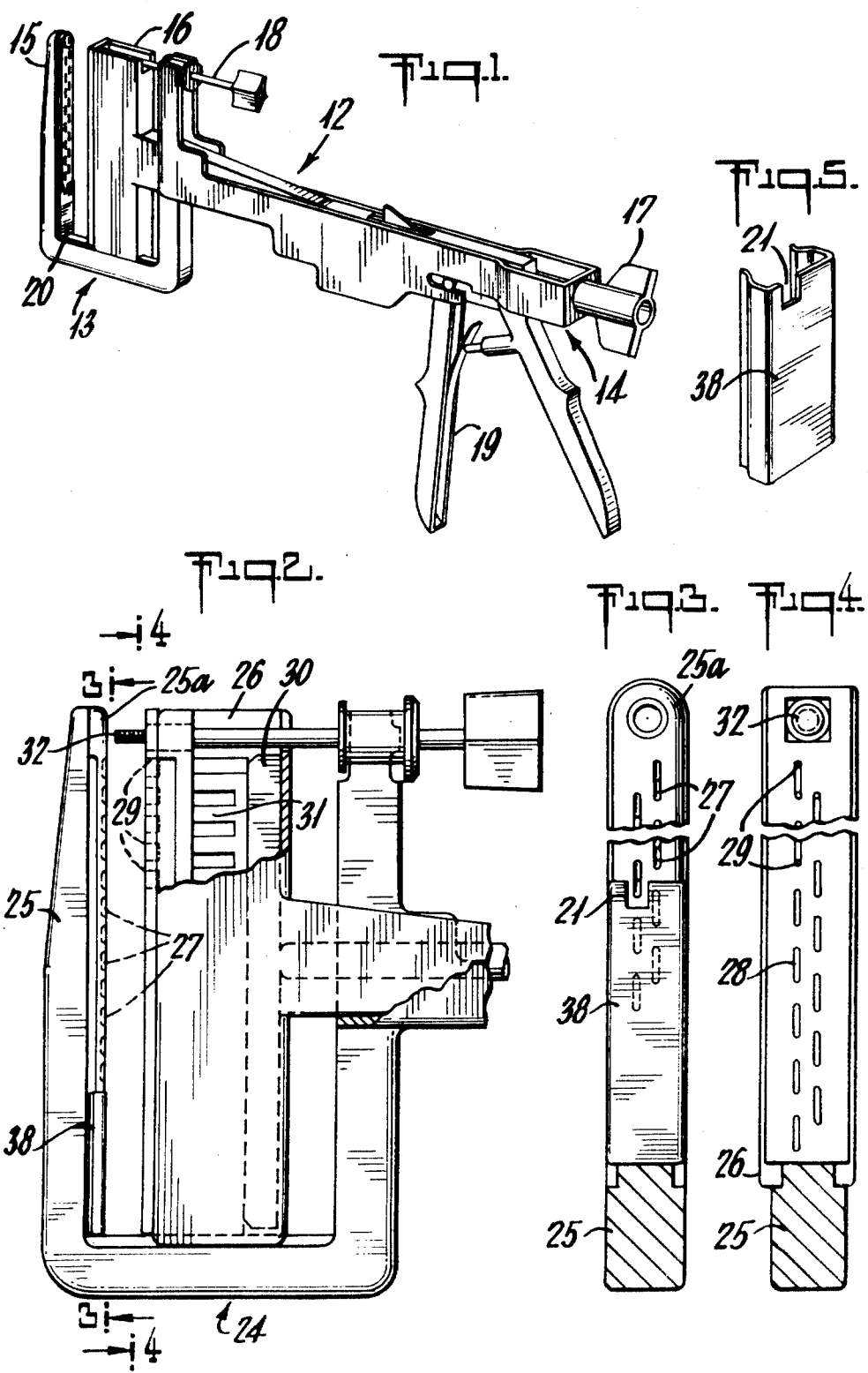

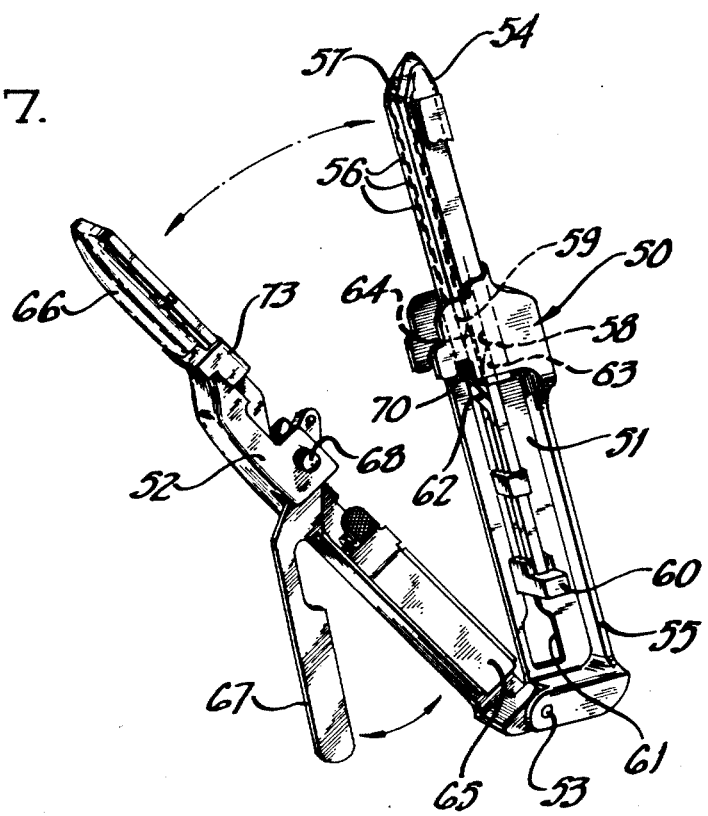
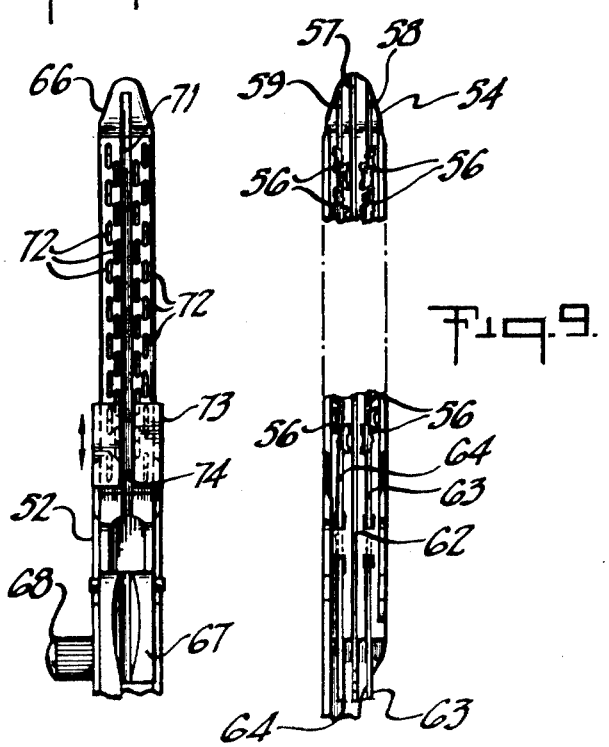

SURGICAL INSTRUMENT FOR SUTURING TISSUES AND ORGANS

The present invention relates to medical instruments and is more particularly concerned with surgical instruments used for suturing or stapling tissues and organs.

BACKGROUND OF THE INVENTION

In various surgical procedures, such as certain abdominal surgical procedures and surgery on the lungs, extensive suturing may be required. In the past, this suturing has been accomplished for the most part by utilizing the standard well known sterile sutures and surgical needles of various types. The suturing procedure is usually time consuming and, hence, requires the patient be kept under anesthesia for considerable lengths of time which, in some instances, may be dangerous. In surgery on the lung, it is often required the lung be collapsed and when repairing this surgery with sutures and needles, it may take a considerable period of time. To aid the patient, it is desired the time the lung is collapsed be kept to a minimum. Also in lung surgery it is difficult to immediately obtain air-tight closures with sutures and needles which, again, may be harmful to the patient or extend the recovery period from the operation. Also, in certain types of abdominal surgery the suturing must be accomplished deep within the abdominal cavity which may be difficult and tedious. Hence, it can be appreciated that a surgical device which can reduce the time for suturing in an operation and simplify the manipulative procedures for both the surgeon and the nurse would be very desirable.

In the recent past, there have been developed a number of types of stapling instruments broadly termed linear staplers. Representative types of such stapling instruments are disclosed and described in U.S. Pat. Nos. 3,252,643, 3,269,630, 3,275,211, 3,494,533, 3,589,589, 3,692,224, 4,272,002, and 4,273,281. Broadly, these instruments describe a supporting jaw or member which is adapted to be located on one side of tissue to be sutured. A working face; i.e., the mechanism carrying the appropriate staples is located on the opposite side of the tissue or organ to be sutured. The instrument includes control means which allows the surgeon to urge the supporting jaw which is going to become the anvil for the staples and the working face which is carrying the staples together to attain an appropriate gap between the anvil and the staple. The staples to be fired are usually disposed in one or more lines of staples along the length of the working face of the instrument. When more than one line is used, the position of the staples is staggered or offset in adjacent lines. Generally, the appropriate firing lever fires all of the staples at once. In some of the instruments, it is possible to fire the staples sequentially starting at one end of the working face and extending to the other end of the face. However, in all of the instruments of the prior art it has been necessary to fire all of the staples in the working face of the instrument. The instruments are made in different sizes to fire different lengths of the line of staple. However, in many surgical procedures, the surgeon will not know exactly what length of staple line will be required until actually at the position of starting to suture the appropriate tissue or organ. Hence, in most surgical procedures, the stapling instrument used will have a working face and supporting jaw longer than that which is required to close the appropriate area. When this happens, the staples not used to close the organ or the tissue are still fired and ejected and left within the surgical site. Presently, the linear stapling devices as they are known provide a fixed length of the staple line generally 30, 55, or 90 millimeters in length. Hence, in use if the incision or the wound to be closed is exactly a distance of 30 or 55 millimeters, you obtain an efficient closure. However, if the wound is 35 millimeters or 40 millimeters in length, you must use the 55 millimeter size stapler. This means a portion of the staples (15 to 20 millimeters) will be discharged by the instrument and deposited in the operative cavity which, as previously mentioned, may be harmful to the patient. On the other hand, if you have a 35 or 40 millimeter incision and you attempt to utilize a 30 millimeter instrument, you will not obtain a complete closure in that you will not obtain hemostatis and hence the smaller instrument cannot be used.

SUMMARY OF THE PRESENT INVENTION

The improved instrument of the present invention allows the surgeon to control the length of the line of staples that will be used to suture the tissue or organ. The instrument of the present invention eliminates the deposition of excess staples within the surgical site or cavity. The instrument of the present invention also allows the surgeon to vary the length of the line of staples he is using to close organs or tissues in a surgical procedure. The surgical instrument of the present invention may be used to suture tissues and organs with staples. The instrument comprises a supporting jaw which is to be located on one side of the tissue or organ to be sutured. The instrument also includes a working face carrying the staples to be inserted into the tissue, which face is to be located on the opposite side of the tissue or organ to be sutured. The instrument also includes means for locating the jaw and the face in a cooperative position whereby at least one line of staples may be applied to the tissue or organ placed between the jaw and the face. The instrument also includes means for actuating the line of staples to insert the staples into the tissue or organ placed between the jaw and the face. Once the staples are inserted, the legs of the staple are clinched by being deformed by an appropriate anvil disposed on the supporting jaw or otherwise secured by an appropriate receiver carried by the supporting jaw. In accordance with the present invention, I have developed an improvement which comprises means for masking a portion of the line of staples to be applied. The masking means is preferably adjustable and in certain embodiments removable. The masking means is adapted to engage and hold the tissue or organ at a length less than the full length of the line of staples.

As previously mentioned, the improvement of the present invention prevents a portion of the line of staples from being discharged in the surgical site. This may be accomplished by making the masking means of a material that accepts the staples when they are actuated; i.e., the material is penetrated by the staple legs and the staple is formed in the masking means rather than in the tissue. In other embodiments of the present invention, this may be accomplished by making the masking means of a material that is not penetratable by the staple legs but instead deforms the staple leg and jams the staple so that it remains in the working face of the instrument. In all of the above-described embodiments, the staples not inserted in the tissue or organ to be sutured remain with the surgical instrument and are removed from the operative site when the instrument is removed from the site.

In either of the above-described embodiments, the masking means may be disposed on the supporting jaw or the working face as desired.

In embodiments of the present invention wherein the staples are fired sequentially the means for preventing a portion of the staples from being discharged into the surgical site may include control means controlling the movement of the sequentially firing member of the instrument. The staples that may be controlled in accordance with the present invention may be a single line of staples or plural lines of staples. When plural lines of staples are used, the staples in adjacent lines are usually either offset or staggered with respect to each other. Also in certain embodiments of my new instrument indicating means may be disposed on the portion of the instrument which the surgeon utilizes to activate the firing of the staples so that the surgeon can determine and be aware of the length of the line of staples that is to be fired or in certain instances that has been fired.

BRIEF DESCRIPTION OF THE DRAWINGS

The invention will be more fully described when taken in conjunction with the accompanying drawings wherein:

FIG. 1 is a perspective view of one type of linear stapling instrument incorporating the improvement of the present invention;

FIG. 2 is a side view of the stapling head of a stapling instrument incorporating the improvement of the present invention;

FIG. 3 is a cross-sectional view taken along line 3—3 of FIG. 2;

FIG. 4 is a cross-sectional view taken along line 4—4 of FIG. 2;

FIG. 5 is an enlarged perspective view of one type of means adapted to fit over either the supporting jaw or the working face of the instrument;

FIG. 7 is a perspective view of yet another type of stapling instrument in accordance with the present invention with potions cut away to aid in describing the instrument;

FIG. 8 is a partial front view showing the anvil member of the instrument depicted in FIG. 7; and FIG. 9 is a partial front view of the staple carrying member of the instrument depicted in FIG. 7.

DETAILED DESCRIPTION OF THE DRAWINGS

Figure 6:
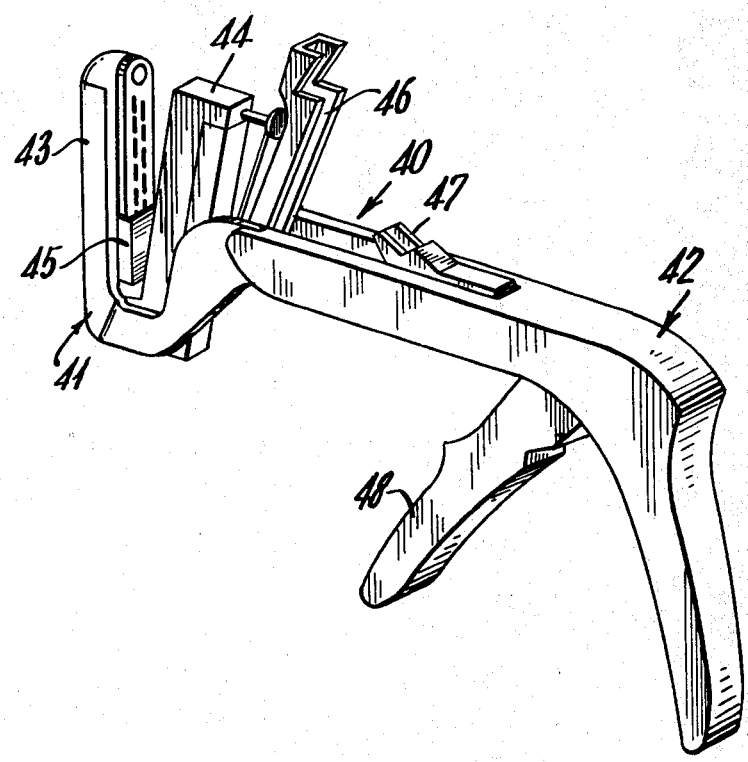
FIG. 6 is a perspective view of another type of disposable stapling instrument in accordance with the present invention.

Referring to the drawings, in FIG. 1 there is shown a linear stapling instrument 12 for suturing tissues and organs. The instrument comprises a tissue engaging section 13 and an application section 14. The tissue engaging section includes supporting jaw 15 which is located on one side of the tissue or the organ to be sutured and working member or face 16 which is situated on the opposite side of the tissue or organ to be sutured. The tissue to be sutured is placed between these two members and the members urged together by appropriate mechanical means such as a screw means actuated by key 17 to urge the working member into closer proximity to the supporting jaw. Once this is accomplished, the members are secured together by a latching means 18 to maintain the face and jaw in position. Once the tissue has been placed between the jaw and face and the jaw and face brought together to an appropriate gap, the working face which carries the staples has the staples fired by an appropriate firing mechanism such as the movement of a ram which ejects the staples from the working face as is well knwon in the art. The firing is accomplished by closing the handle 19. The supporting jaw carries a removable and adjustable masking means 20 which covers part of the supporting jaw. The masking means may come in various sizes to accomodate different tissue sizes. The masking means may be placed on the supporting jaw or on the working face as desired. The masking means may be placed on either the jaw or face at anytime prior to the firing of the staples.

As is more clearly shown in FIGS. 2, 3, and 4, the tissue engaging section 24 of the instrument comprises the supporting jaw 25 and the working face 26. The supporting jaw carries an anvil 25a for metal staples. As is seen in FIG. 3, the anvil has a plurality of depressions 27 which are used to form the staples by clinching the staple legs as is well known. The staples 29 are in a pair of longitudinal rows of openings 28 with the openings offset and in a pattern corresponding to the depressions in the anvil. Each opening carries a staple 29 and behind the staple is a movable ram 30 which has drive extensions 31 with each extension engaging a staple. In use, the length of the incision or wound to be sutured is determined. The removable and adjustable masking means 38 shown in FIG. 5 is made of a suitable pliable plastic material which may be easily cut with scissors or a knife to the desired length. If desired, the plastic masking means may be perforated at spaced apart areas along the means to allow the means to be easily broken apart in order to attain the desired size of the means. The masking means may be placed on either the supporting jaw of the working face of the instrument as desired. It is preferred that the masking means include an indented area 21 so the means may be positioned over a full staple when used with an instrument having a plurality of rows of staples with the staples offset in adjacent rows, as is more clearly shown in FIG. 3. The masking means is placed at either the bottom or the top of the anvil member so that just the right length of the supporting face is or will be in contact with the tissue. The tissue is placed in abutting relationship to the masking means and adjacent the support jaw. By abutting the tissue to the masking means the tissue is, of course, stabilized and aided in being held in position between the supporting jaw 25 and the working face 26. In many instances it may be easier to place the tissue between the supporting jaw and working face first and then abut the masking means to the tissue. The latching mechanism 32 is secured and the working face urged towards the supporting jaw until the appropriate gap is attained. The staples are fired and pushed through the tissue and their legs clinched. The staples fired in that portion of the line not closing the tissue are fired into the masking means and are removed when the instrument is removed from the operative site.

Referring to FIG. 6 there is shown a disposable linear surgical stapler 40 in accordance with the present invention. In this embodiment, the surgical stapler comprises a working or tissue engaging portion 41 and the actuating or control portion 42. The working portion 41 comprises a supporting jaw 43 which is the anvil for metal staples and a working member or face 44 which comprises the staples themselves and the drive means for driving the staples. In this embodiment, the working member carries a masking means 45 which is telescopically adjustable to control the length of the line of staples that is to be placed in the tissue. In use, the tissue is placed between the supporting jaw 43 and the working member 44. A lever 46 is brought down to urge the working member towards the supporting jaw end and is engaged by lock 47 to attain the appropriate gap between the jaw and member to set the staples. The masking means is placed adjacent the tissue and the staples fired by pulling the pistol grip 48 which fires the staples into the tissue and the anvil clinchs the staple legs. The staples not set into the tissue are deformed by the masking means and remain jammed in the surgical stapler and are disposed of with the instrument.

In FIGS. 7, 8, and 9 there is depicted another type of surgical stapling instrument 50. This instrument is primarily used in performing gastro-intestinal anastamosis. The instrument comprises a staple driving and cutting member 61 and an anvil member 52. The two members are pivotally connected at their distal ends by a pivot pin 53. The staple driving and cutting member comprises a staple holding and driving head 54 or working face connected to a handle section 55. Disposed in the staple holding and driving head are four rows of staple openings 56 with two rows on either side of a longitudinally extending open channel 57. The staple openings in adjacent rows are offset. Behind the rows of staple openings on opposite sides of the open channel are a pair of channels 58 and 59 for accepting staple drivers. A slideable member 60 is guideably disposed in a cutout 61 extending substantially the length of the handle section. Attached to the slideable member is a cutting knife 62 disposed to slide substantially the entire length of the longitudinally extending open channel 57 between the rows of staples. Disposed from the slideable member on opposite sides of the knife and extending just in front of the knife are a pair of staple drivers 63 and 64. The staple drivers are slideable in the channels 58 and 59.

The anvil member 52 comprises a handle section 65 from which the anvil head 66 or supporting jaw extends. The handle section is pivotally mounted to the handle section of the staple driving and cutting member as previously described. The handle section includes a locking member 67 pivotally connected just behind the anvil head by a pivot pin 68. The locking member is adapted to interlock with the handle section of the staple driving and cutting member by a pin 69 at the end of the locking member engaging with an indent 70 in the staple driving and cutting member. The anvil head includes a longitudinal channel 71 extending the length of the head. Four rows of anvil depressions 72 are disposed in the head with two rows on each side of the longitudinal channel. The anvil depressions are disposed to cooperate with the staples in the staple holding and driving head is well-known. The anvil head carries a masking means 73 which snaps over the anvil head. The masking means has a slit 74 running along its length aligned with the longitudinal channel in the anvil head. The masking means is made of a plastic material that may be easily cut with scissors.

In use, the staple driving and cutting member and the anvil member are moved apart and the tissue to be stapled and cut placed between the staple holding and driving head and the anvil head. The masking means is sized so that the length of the anvil depressions left unmasked is the same as the length of tissue to be stapled and the masking means placed on the anvil head. The staple holding and driving head and anvil head are placed adjacent and the handles locked together by inserting the pin into the indented portion and pivoting the locking member towards the handle section of the staple driving and cutting member. After the two members are locked together, the slideable member is moved along the cutout in the handle section pushing the staple drivers through the channels behind the staple openings driving the staples through the tissue into the anvil depressions setting the staples in all the tissue with the unrequired staples being set in the masking means. Immediately after the staples are set, the cutting knife severs the tissue between the two center staple rows. The staple driving and cutting member and the anvil member are disengaged and removed from the tissue leaving cut and stapled adjacent tissue sections.

Though I have shown a pistol type of actuating mechanism various other actuating mechanism well known in the art may also be used; such as, hypodermic or syringe type of mechanism, a turn key or winding mechanism and the like.

The masking means for the instrument may be made from suitable plastic materials such as polyethylene or the like which may be injected molded or compression molded or otherwise produced in the desired configuration. The means should be resilient so that it may be deformed and readily snap on and off the appropriate portions of the instruments.

In embodiments of the instrument of the present invention wherein it is desired to deform the staple legs, the masking means may be made of a metal such as stainless steel or the like.

Having now described the present invention and various embodiments, it will be readily apparent to one skilled in the art that other variations, modifications and alterations may be made to the present invention without departing from the spirit and scope thereof.

What is claimed is:

1. In a surgical instrument for suturing tissues and organs with at least one line of staples, said instrument comprising a supporting jaw to be located on one side of the tissue or organ to be sutured, a working face to be located on the opposite side of the tissue or organ to be sutured, means for locating said jaw and face in a cooperative position whereby at least one line of staples may be applied to the tissue or organ to be sutured, and means for actuating said line of staples to insert them into the tissue or organ placed between the jaws and face, the improvement comprising means for masking a portion of the line of staples so that a portion of the line of staples remain with the surgical instrument after said line of staples has been actuated.

2. The improvement according to claim 1 wherein the masking means assists in stabilizing the tissue placed between the supporting jaw and working face.

3. The improvement according to claim 1 or 2 wherein the masking means is adjustable so as to vary the portion of the line of staples that remain with the instrument.

4. The improvement according to claim 1, or 2 wherein the masking means is made of a material that is penetratable by the staple legs whereby the staples are inserted in the masking means.

5. The improvement according to claim 4 wherein the masking means is disposed on the supporting jaw of the surgical instrument.

6. The improvement according to Claim 1, or 2 wherein the masking means is made of a material that deforms the staple legs whereby the staples remain in the working face of the instrument.

7. The improvement according to Claim 6 wherein the masking means is disposed on the supporting jaw of the surgical instrument.

8. The improvement according to Claim 1 or 2 wherein the masking means is removably attached to the supporting jaw of the instrument.

9. The improvement according to Claims 1 or 2 wherein the masking means is removably attached to the working face of the instrument.

10. The improvement according to Claim 4 wherein the masking means is adjustable so as to vary the portion of the line of staples that remain with the instrument.

11. The improvement according to Claim 6 wherein the masking means is adjustable so as to vary the portion of the line of staples that remain with the instrument.

* * * * *